US00PP19542P2

(12) United States Plant Patent
The

(10) Patent No.: US PP19,542 P2
(45) Date of Patent: Dec. 2, 2008

(54) ***ABUTILON* PLANT NAMED 'ABU001'**

(50) Latin Name: ***Abutilon megapotamicum*×*Abutilon* hybrid**
Varietal Denomination: ABU001

(75) Inventor: Dante The, Cheltenham (AU)

(73) Assignee: Ian M. Collins, Canoelands, NSW (AU)

( * ) Notice: Subject to any disclaimer, the term of this patent is extended or adjusted under 35 U.S.C. 154(b) by 0 days.

(21) Appl. No.: 11/978,497

(22) Filed: Oct. 29, 2007

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Kent L Bell
(74) *Attorney, Agent, or Firm*—C. A. Whealy

(57) ABSTRACT

A new and distinct cultivar of *Abutilon* plant named 'ABU001', characterized by its compact, upright and mounded growth habit; vigorous growth habit; freely branching habit; freely flowering habit; yellow-colored flowers; and good garden performance.

1 Drawing Sheet

Botanical designation: *Abutilon megapotamicum*× *Abutilon* hybrid.
Cultivar denomination: 'ABU001'.

BACKGROUND OF THE INVENTION

The present invention relates to a new and distinct cultivar of *Abutilon,* botanically known as *Abutilon megapotamicum*×*Abutilon* hybrid and hereinafter referred to by the name 'ABU001'.

The new *Abutilon* is a product of a planned breeding program conducted by the Inventor in Cheltenham, New South Wales, Australia. The objective of the breeding program is to create new compact *Abutilon* cultivars with numerous flowers.

The new *Abutilon* originated from a cross-pollination made by the Inventor in 1996 in Cheltenham, New South Wales, Australia of an unnamed selection of *Abutilon megapotamicum,* not patented, as the female, or seed, parent with an unnamed selection of *Abutilon* hybrid, not patented, as the male, or pollen, parent. The new *Abutilon* was discovered and selected by the Inventor as a single flowering plant within the progeny of the stated cross-pollination in a controlled environment in Cheltenham, New South Wales, Australia in 1997.

Asexual reproduction of the new *Abutilon* by cuttings in a controlled environment in Cheltenham, New South Wales, Australia since 1998, has shown that the unique features of this new *Abutilon* are stable and reproduced true to type in successive generations.

SUMMARY OF THE INVENTION

The cultivar ABU001 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'ABU001'. These characteristics in combination distinguish 'ABU001' as a new and distinct cultivar of *Abutilon:*

1. Compact, upright and mounded growth habit.
2. Vigorous growth habit.
3. Freely branching habit.
4. Freely flowering habit.
5. Yellow-colored flowers.
6. Good garden performance.

Plants of the new *Abutilon* can be compared to plants of the parent selections. Plants of the new *Abutilon* differ from plants of the parent selections primarily in growth habit as plants of the new *Abutilon* are more vigorous than plants of the parent selections.

Plants of the new *Abutilon* can also be compared to plants of the *Abutilon* cultivar Moonchimes, not patented. Plants of the new *Abutilon* differed from plants of the cultivar Moonchimes primarily in growth habit as plants of the new *Abutilon* are more compact and uniform than plants of the cultivar Moonchimes.

BRIEF DESCRIPTION OF THE PHOTOGRAPHS

The accompanying colored photographs illustrate the overall appearance of the new *Abutilon,* showing the colors as true as it is reasonably possible to obtain in colored reproductions of this type. Colors in the photographs may differ slightly from the color values cited in the detailed botanical description which accurately describe the colors of the new *Abutilon.*

The photograph at the bottom of the sheet comprises a side perspective view of a typical plant of 'ABU001' grown in a container.

The photographs at the top of the sheet are close-up views of typical flowers of 'ABU001'.

DETAILED BOTANICAL DESCRIPTION

The photograph and following observations, measurements and values describe plants grown in Bonsall, Calif. during the spring in a polyethylene-covered greenhouse and conditions which approximate commercial *Abutilon* production. During the production of the plants, day temperatures ranging from 13° C. to 38° C. and night temperatures ranging from 13° C. to 21° C. Rooted young plants had been growing for about twelve weeks with three plants per one-gallon container when the photographs and description were taken. In the following description, color references are made to The Royal Horticultural Society Colour Chart, 1995 Edition, except where general terms of ordinary dictionary significance are used.

Botanical classification: *Abutilon megapotamicum*×*Abutilon* hybrid cultivar ABU001.

Parentage:

*Female, or seed, parent.*—Unnamed selection of *Abutilon megapotamicum,* not patented.

*Male, or pollen, parent.*—Unnamed selection of *Abutilon* hybrid, not patented.

Propagation:

*Type.*—By cuttings.

*Time to initiate roots.*—About two to three weeks.

*Time to produce a rooted young plant.*—About four weeks.

*Root description.*—Fibrous.

*Rooting habit.*—Freely branching; moderately dense.

Plant description:

*Plant and growth habit.*—Compact, upright and mounded growth habit. Freely branching habit with about five primary lateral branches and numerous secondary lateral branches developing per plant; dense and bushy habit. Vigorous growth habit.

*Plant height.*—About 35 cm.

*Plant diameter.*—About 48 cm.

Lateral branch description:

*Length.*—About 25 cm.

*Diameter.*—About 4 mm.

*Internode length.*—About 1.7 cm.

*Texture.*—Smooth, glabrous.

*Color.*—Young stems, 144A; older stems, more grey than 148A.

Foliage description:

*Arrangement.*—Alternate; simple.

*Length.*—About 5.5 cm.

*Width.*—About 4.4 cm.

*Shape.*—Elliptic with three lobes.

*Apex.*—Acute.

*Base.*—Cordate.

*Margin.*—Irregularly serrate.

*Texture, upper surface.*—Smooth, glabrous; leathery.

*Texture, lower surface.*—Pubescent; slightly grainy.

*Venation pattern.*—Palmate; reticulate.

*Color.*—Developing foliage, upper surface: 144A. Developing foliage, lower surface: 148B. Fully developed foliage, upper surface: 147A; venation, 147B. Fully developed foliage, lower surface: 147B; venation, 147C.

*Petiole length.*—About 2.5 cm.

*Petiole diameter.*—About 1 mm.

*Petiole texture, upper and lower surfaces.*—Smooth, glabrous.

*Petiole color, upper surface.*—200B to 200C.

*Petiole color, lower surface.*—144A.

Flower description:

*Flower arrangement and habit.*—Single campanulate axillary flowers. Freely flowering habit with about 18 flowers and flowers buds per lateral stem. Flowers not persistent. Flowers pendulous.

*Fragrance.*—None detected.

*Natural flowering season.*—Plants flower continuously from the spring until the fall in Southern California.

*Flower longevity.*—Individual flowers last about seven days on the plant.

*Flower diameter.*—About 5.3 cm.

*Flower depth* (*height*).—About 3.8 cm.

*Flower bud.*—Shape: Ovoid. Length: About 1.8 cm. Diameter: About 1.2 cm. Color: 10A.

*Petals.*—Arrangement: Five in a single whorl. Length: About 3.8 cm. Width: About 3 cm. Shape: Obovate. Apex: Obtuse. Margin: Entire. Texture, upper and lower surfaces: Smooth, glabrous. Color: When opening, upper surface: 10A. When opening, lower surface: 10B. Fully opened, upper surface: 11A. Fully opened, lower surface: 11B.

*Sepals.*—Arrangement: Five in a single whorl fused at the base; calyx, campanulate. Length: About 8 mm. Width: About 6 mm. Shape: Elliptic. Apex: Acute. Margin: Entire. Texture, upper and lower surfaces: Pubescent. Color, upper and lower surfaces: 145A to 145B.

*Peduncles.*—Length: About 3.4 cm. Diameter: About 1 mm. Strength: Strong. Texture: Smooth, glabrous. Color: 144B.

*Reproductive organs.*—Stamens: Quantity per flower: About 150. Anther length: Less than 1 mm. Anther shape: Rounded. Anther color: 13B. Pollen amount: Scarce to moderate. Pollen color: 13B. Pistils: Quantity: One per flower. Pistil length: About 3.8 cm. Style length: About 3 cm. Style color: 10D. Stigma shape: Rounded. Stigma color: 10B. Ovary color: 145D. Seed/fruit: Seed and fruit development have not been observed on plants of the new *Abutilon.*

Garden performance: Plants of the new *Abutilon* have been observed to have good garden performance and tolerate wind, rain and temperatures ranging from about 0° C. to about 35° C.

Pathogen/pest resistance: Plants of the new *Abutilon* have not been observed to be resistant to pathogens and pests common to *Abutilon.*

It is claimed:

1. A new and distinct *Abutilon* plant named 'ABU001' as illustrated and described.

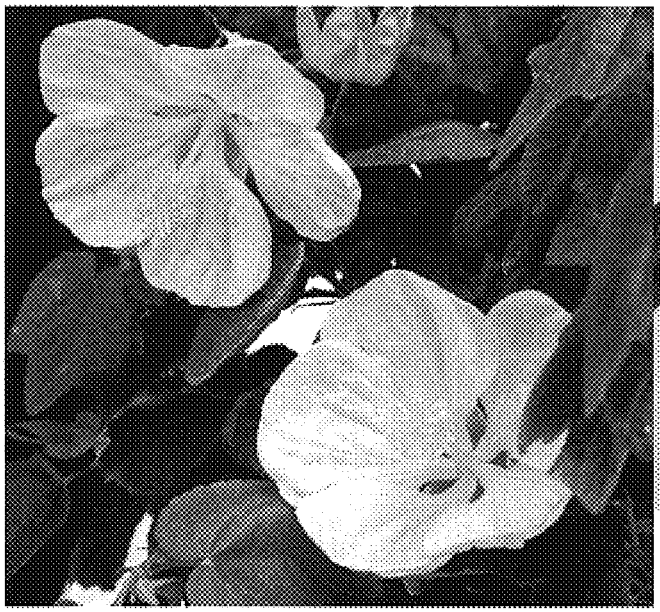
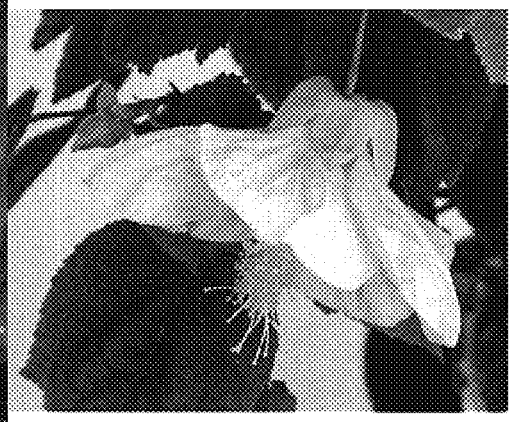
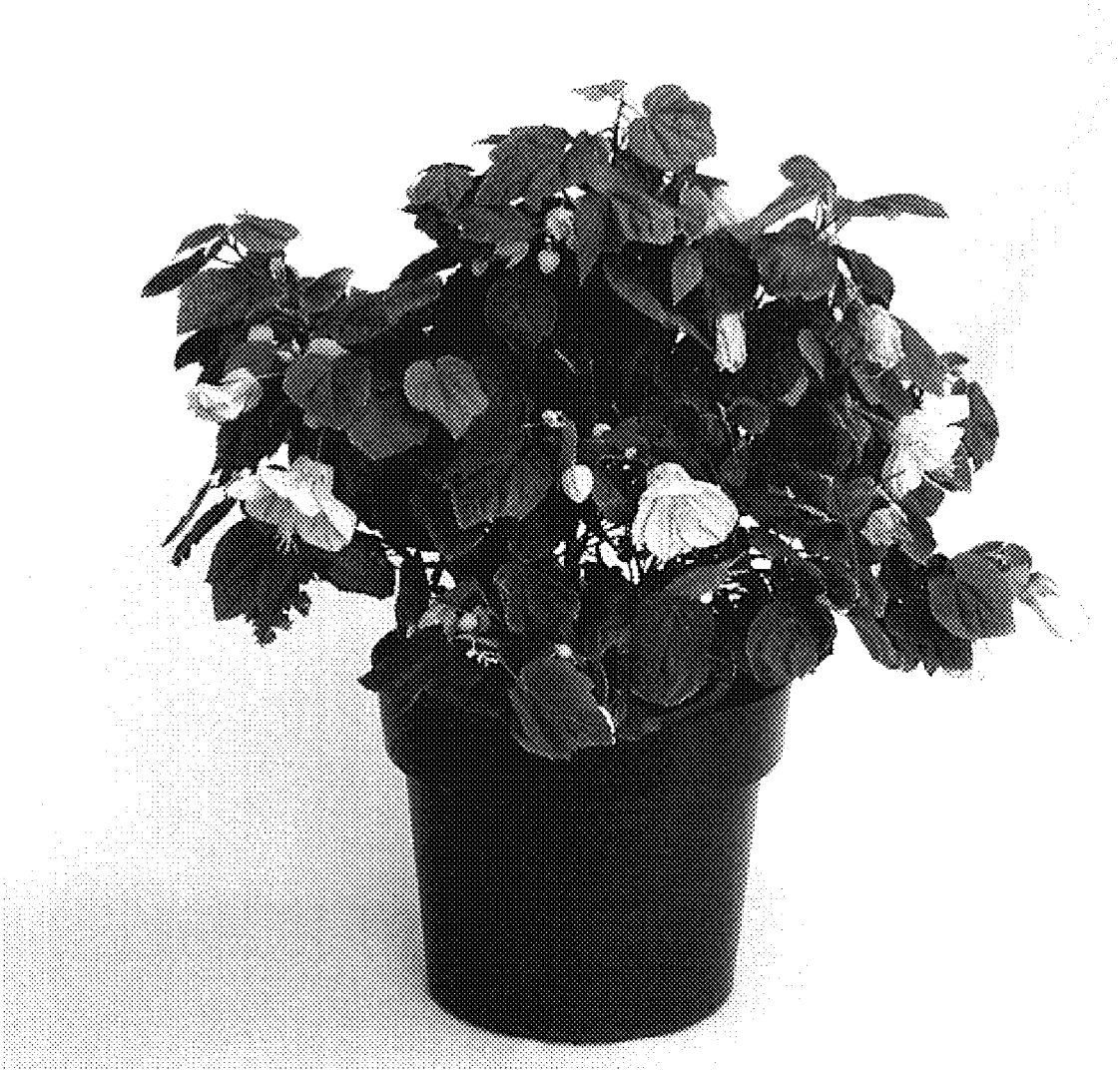

* * * * *